United States Patent [19]

Hasson et al.

[11] Patent Number: 5,176,697

[45] Date of Patent: * Jan. 5, 1993

[54] LAPAROSCOPIC CANNULA

[76] Inventors: Harrith M. Hasson, 2043 N. Sedgwick, Chicago, Ill. 60614; Scott C. Marlow, 12441 Bentbrook Dr., Chesterland, Ohio 44026; Herbert F. D'Alo, 37 Forest Hills Dr., Madison, Conn. 06443; Clifford A. Marlow, 35469 Ridge Rd., Willoughby, Ohio 44094

[*] Notice: The portion of the term of this patent subsequent to Mar. 26, 2008 has been disclaimed.

[21] Appl. No.: 590,354

[22] Filed: Sep. 28, 1990

Related U.S. Application Data

[63] Continuation-in-part of Ser. No. 334,452, Apr. 16, 1989, Pat. No. 5,002,557.

[51] Int. Cl.$^5$ .................................... A61M 37/00
[52] U.S. Cl. ...................................... 606/191; 604/26; 604/42; 604/174
[58] Field of Search ............. 606/13, 14, 96, 108, 606/191, 119; 128/747, DIG. 26, 454; 604/49, 51, 96, 98, 178, 174, 175, 42, 95, 272–274, 264, 102, 103, 283

[56] References Cited

U.S. PATENT DOCUMENTS

| | | |
|---|---|---|
| 3,039,468 | 6/1962 | Price . |
| 3,253,594 | 5/1966 | Matthews et al. .......... 128/DIG. 26 |
| 3,459,175 | 8/1969 | Miller . |
| 3,817,251 | 6/1974 | Hasson .......................... 604/174 X |
| 4,077,412 | 3/1978 | Moossun . |
| 4,379,458 | 4/1983 | Bauer et al. ...................... 604/264 |
| 4,535,773 | 8/1985 | Yoon .................................. 604/51 |
| 4,540,404 | 9/1985 | Wolvek ............................... 604/96 |

Primary Examiner—Robert A. Hafer
Assistant Examiner—Kerry Owens
Attorney, Agent, or Firm—Wood, Phillips, VanSanten, Hoffman and Ertel

[57] ABSTRACT

A cannula for extension through a tissue into a cavity and having: a cylindrical sleeve defining a hollow passageway through which a surgical instrument can be directed, with the sleeve having a) a proximal end to be manipulated by a user in directing the sleeve into an operative position through the body tissue into the body cavity, b) a distal end which projects into the body cavity with the sleeve in its operative position, and c) a cylindrical outer surface; expandable structure at the distal end of the sleeve for preventing withdrawal of the sleeve from the tissue with the expandable structure in an expanded state, the expandable structure being collapsible from its expanded state, wherein it projects radially beyond the outer surface of the sleeve sufficiently to prevent passage of the distal end of the sleeve and expandable structure thereon through an incision having a diameter approximately equal to the diameter of the outer cylindrical surface of the sleeve, to a collapsed state in which the expandable structure does not project sufficiently beyond the outer surface of the sleeve to significantly obstruct passage of the distal end of the sleeve and expandable structure through a tissue incision approximately equal in diameter to the outer surface of the sleeve; structure for selectively placing the expandable structure in its expanded and collapsed states; a retaining collar having a tapered surface; and cooperating structure on the sleeve and collar for permitting movement of the collar relative to the sleeve towards the sleeve distal end so that the body tissue through which the sleeve is directed can be captured between the tapered collar surface and the expandable structure to thereby maintain the sleeve positively in its operative position.

21 Claims, 3 Drawing Sheets

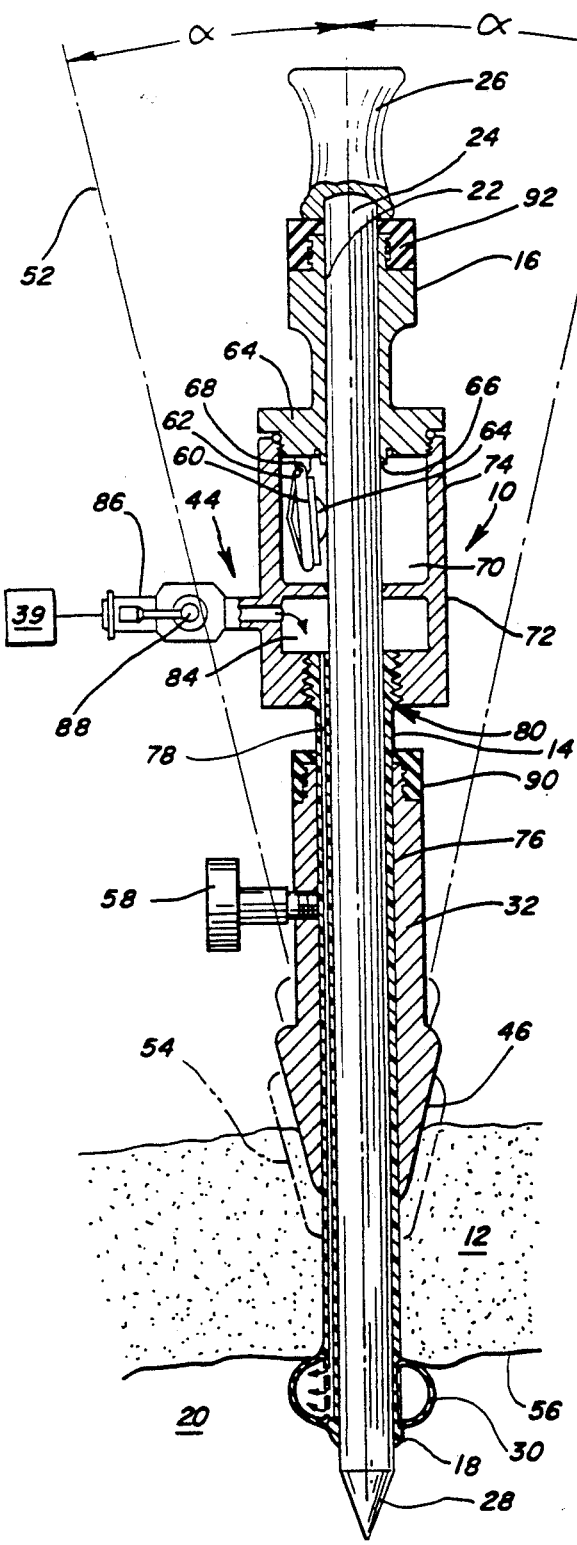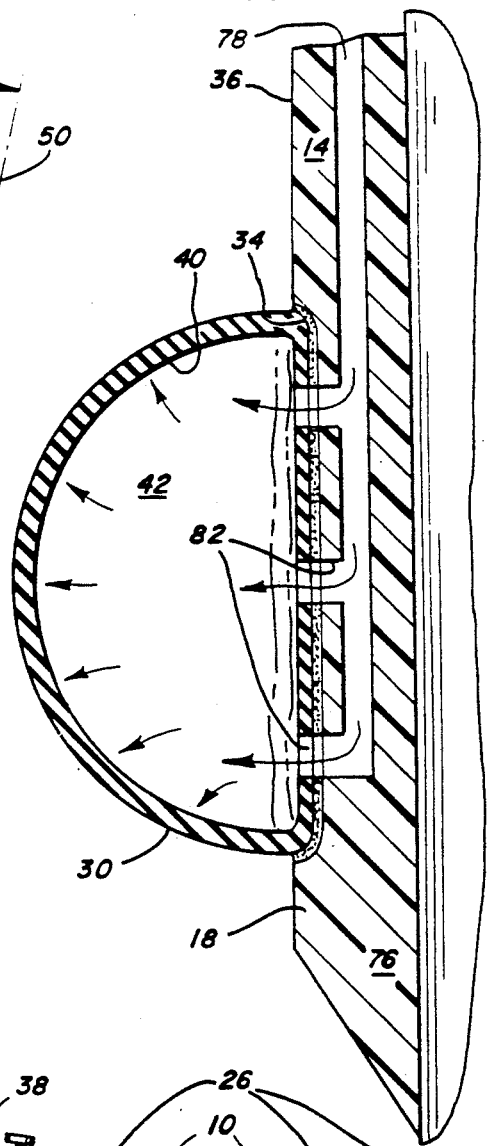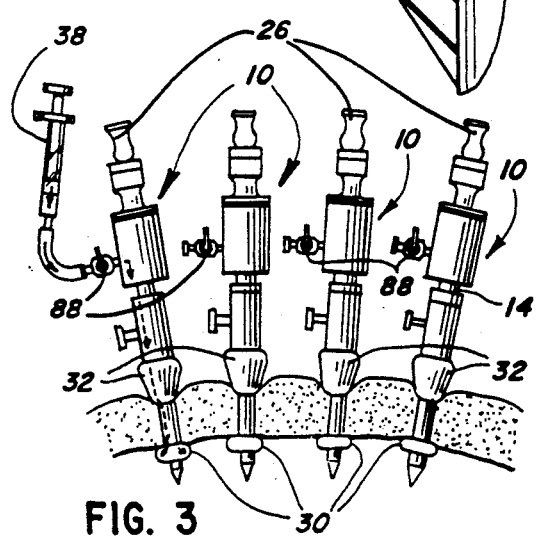

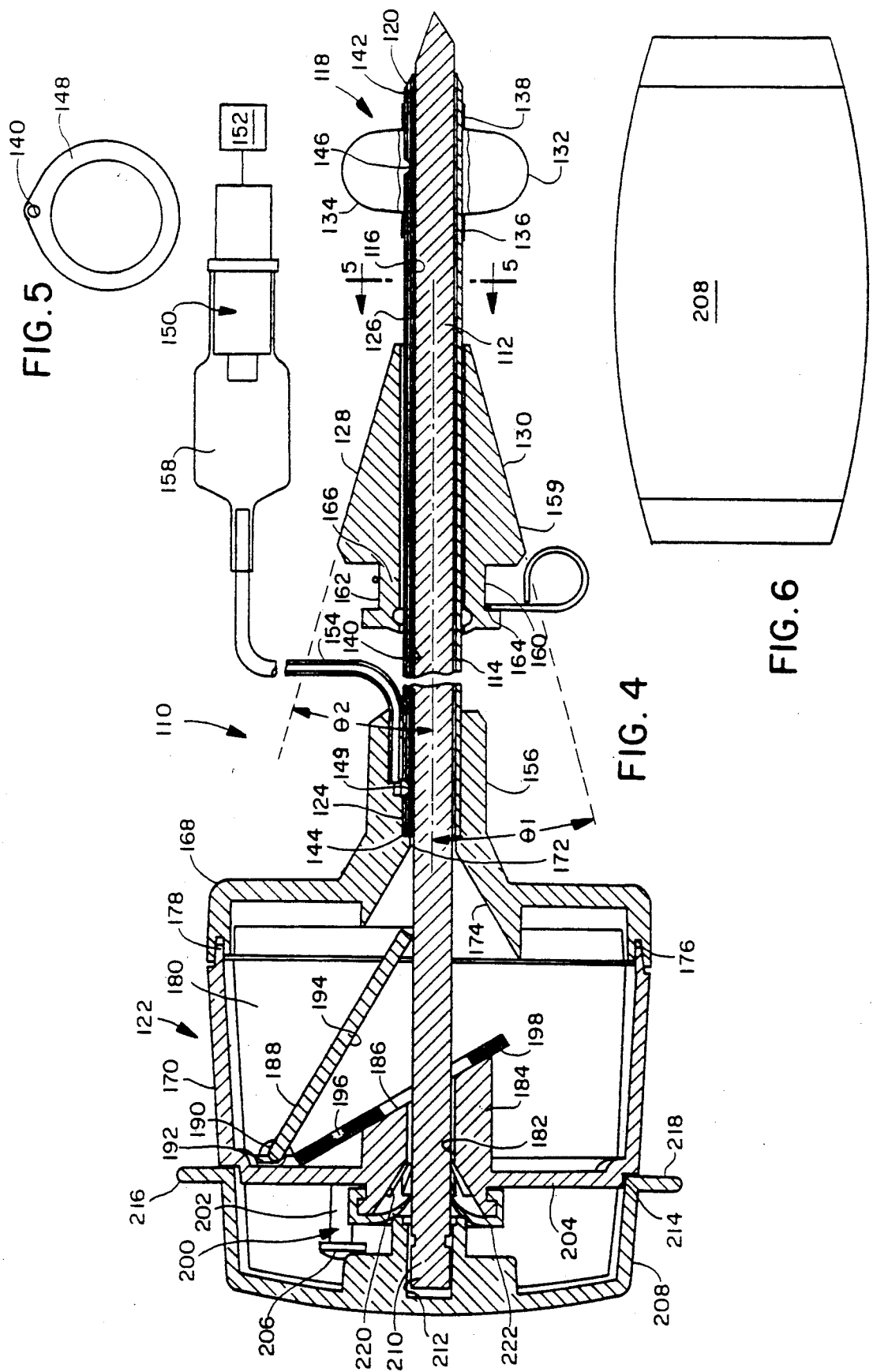

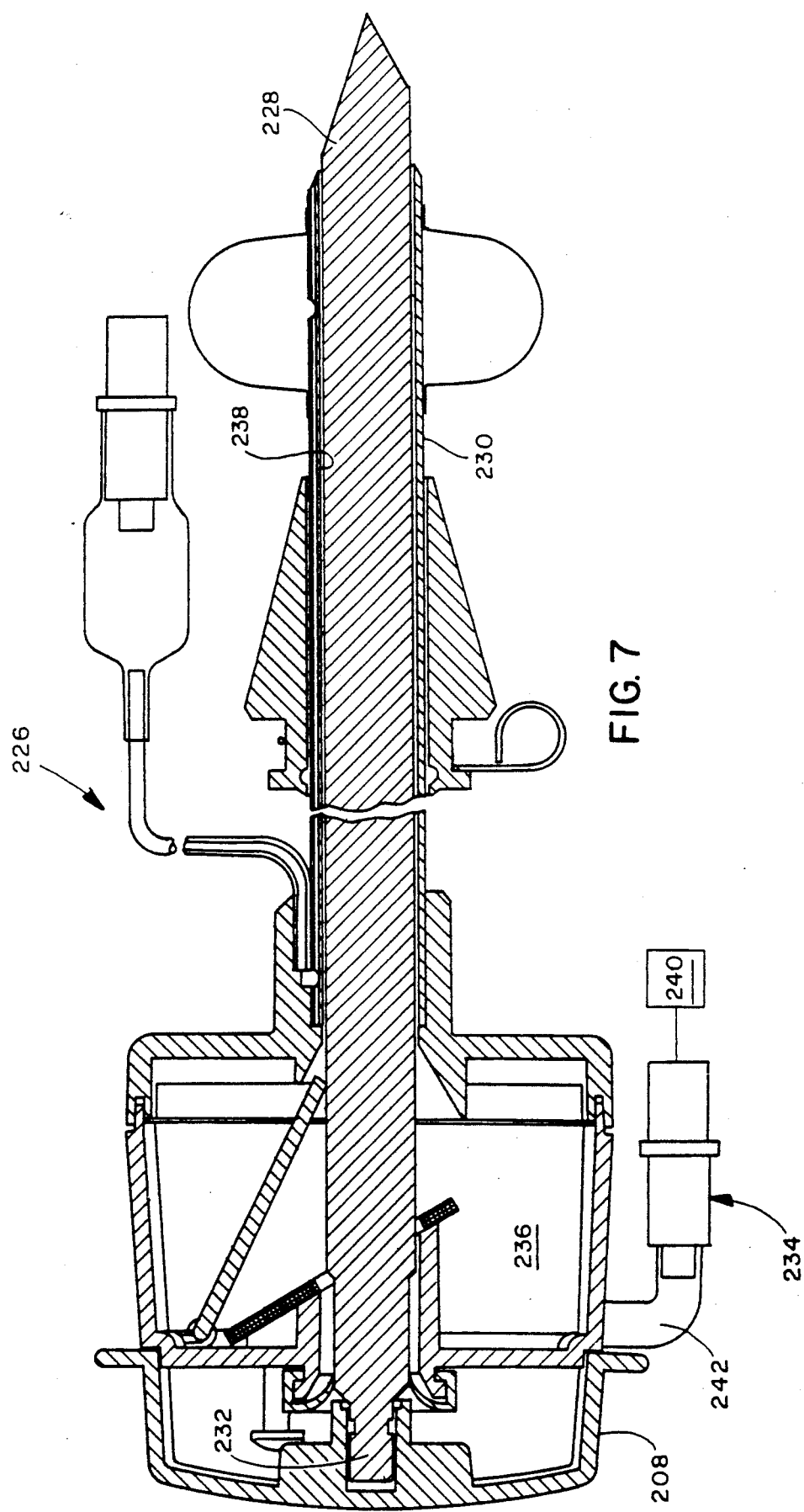

1

LAPAROSCOPIC CANNULA

CROSS-REFERENCE

This application is a continuation-in-part of application Ser. No. 334,452, filed Apr. 16, 1989, now U.S. Pat. No. 5,002,557, entitled "Laparoscopic Cannula".

BACKGROUND OF THE INVENTION

1. Field of the Invention

This invention relates to cannulas of the type used to perform laparoscopic surgery and, more particularly, to structure for maintaining a cannula in operative position with respect to body tissue through which the cannula extends.

2. Background Art

In performing laparoscopic surgery, an incision is made in a patient to admit a cannula which serves as a conduit for the introduction of selected surgical instruments into a body cavity. During a surgical procedure, several cannulas may be directed into the patient at spaced locations to facilitate simultaneous use of a number of instruments. The body cavity in which the operation is performed is filled with a gas to expand the surrounding tissue to create a suitably sized operating space.

In designing laparoscopic equipment, there are several objectives. First, it is important to confine the gas used to expand the cavity in which the operation is to be performed with the cannula in operative position. Deflation of the body cavity could result in interruption of a surgical procedure and/or injury to the patient's internal organs.

It is also important that the cannula be positively maintained in its operative position on the body tissue through which it passes. By positively positioning the cannulas, internal and external clashing between multiple instruments is minimized.

A further objective is to permit the cannula, in its operative position, to be reoriented with respect to a cavity to maximize the working range for each instrument and thereby minimize the number of cannulas that must be used.

Generally, the above three objectives are competing. For example, by positively maintaining the cannula in its operative position, the leakage of gas may be minimized, however the range of motion for the instrument extending through the cannula may be limited.

Examples of prior art structures utilized to maintain a cannula in an operating position with respect to tissue through which the cannula extends are shown in each of U.S. Pat. Nos. 3,039,468, to Price; 3,253,594, to Matthews et al; 3,459,175, to Miller; and 4,077,412, to Moossun. In each of the above four patents, a disk with a large surface area is borne against one side of a tissue through which the cannula extends to thereby positively maintain the position of the cannula. The large contact area between the disks and tissue minimizes the amount of permissible repositioning of the cannula with respect to the tissue. Further, if the disk is brought sufficiently tightly against the tissue to maintain the position of the cannula, the underlying tissue may be traumatized.

There is another drawback with prior art structures utilizing an inflatable balloon/membrane to maintain the cannula in operative position. With such devices, a balloon is inflated to provide an obstruction to removal of the cannula from an incision. A tube/conduit is required to selectively inflate and deflate the balloon from a point externally of the body.

Exemplary prior art conduits are shown in U.S. Pat. Nos. 3,253,594, to Matthews et al and 3,459,175, to Miller. In each, the exposed conduit is separately passed through an incision in the body tissue. The opening for the conduits affords another escape route for gas within the cavity. The conduits are also prone to being severed or pinched. Further, the conduits are difficult to clean and potentially unsanitary when reused.

The present invention is specifically directed to overcoming the above-enumerated problems in a novel and simple manner.

SUMMARY OF THE INVENTION

According to the invention a laparoscopic cannula is provided having a sleeve defining a hollow passageway through which a surgical instrument can be directed and having a proximal end and a distal end which projects into a cavity with the sleeve in its operative position, expandable structure at the distal end of the sleeve which is selectively expandable and collapsible and which prevents withdrawal of the sleeve in its expanded state, structure for selectively expanding and collapsing the expandable structure, a retaining collar with a tapered surface, and cooperating structure on the sleeve and collar for permitting movement of the collar relative to the sleeve towards the sleeve distal end whereby body tissue through which the sleeve is directed can be captured between the tapered collar surface and expandable structure to maintain the sleeve in its operative position.

The tapered collar surface is caused to penetrate the body tissue and thereby maintain a leakproof seal around the incision. The collar does not have to be squeezed tightly against the body tissue to effect this seal and thus the possibility of local traumatization is minimized.

In a preferred form of the collar, the tapered surface thereon defines a truncated cone with the surface making an angle of preferably approximately 15° or greater with respect to the cone axis.

Further, the collar and expandable structure permit a significant amount of reorientation of the cannula in its operative position without compromising the integrity of the seal at the incision.

At the same time, the cannula is sufficiently positively maintained in its operative position so as to minimize internal and external clashing of instruments and facilitate placement in and removal of instruments from the body cavity through the cannula passageway.

Preferably, the expandable structure is a flexible membrane which surrounds the distal end of the sleeve. In a preferred form, the membrane is made from polyethylene teraphthalate which is sufficiently durable to resist rupture and positively prohibit withdrawal of the cannula from an incision. The material is nonetheless sufficiently flexible to permit significant reorientation of the cannula during an operation.

Another aspect of the invention is the provision of structure to block the passage of gas through the cannula passageway at times when there is no instrument in the cannula. In one exemplary embodiment, a hinged door is provided on the cannula and is engaged and opened by an instrument directed through the cannula passageway. Upon the instrument being withdrawn, a spring urges the door back to its closed/sealing position.

Another aspect of the invention is the formation of the sleeve in at least two parts. In a preferred form, one sleeve part defines at least part of a conduit that is used to direct air against the membrane/balloon to effect inflation thereof and to exhaust air to collapse the membrane/balloon. The one sleeve part can be made by extrusion and preferably of plastic or fiberglass so as to be a low cost, disposable item. In a preferred form, the one sleeve part is threadably mated with a second sleeve part having the door to block the cannula passageway. The result is that the relatively expensive second part of the cannula, generally made at least in part from medical grade stainless steel, which remains externally of the patient, can be reused, whereas that part of the cannula that penetrates the patient can be disposed of and readily replaced.

The one sleeve part can be made in different lengths which can be selected depending upon the particular type of surgery and patient.

In a preferred form, the collar is designed to be removably slid over the first sleeve part and has a set screw to fix the position of the collar on the sleeve. The collar can be separated from the disposable first sleeve part and replaced on another like disposable sleeve part to cooperate with the reusable sleeve part.

In a preferred form, each of the first and second sleeve parts defines a part of the sleeve passageway.

Still further, according to the present invention, a cannula is provided for extension through a tissue into a cavity and having: a cylindrical sleeve defining a hollow passageway through which a surgical instrument can be directed, with the sleeve having a) a proximal end to be manipulated by a user in directing the sleeve into an operative position through the body tissue into the body cavity, b) a distal end which projects into the body cavity with the sleeve in its operative position, and c) a cylindrical outer surface; expandable structure at the distal end of the sleeve for preventing withdrawal of the sleeve from the tissue with the expandable structure in an expanded state, the expandable structure being collapsible from its expanded state, wherein it projects radially beyond the outer surface of the sleeve sufficiently to prevent passage of the distal end of the sleeve and expandable structure thereon through an incision having a diameter approximately equal to the diameter of the outer cylindrical surface of the sleeve, to a collapsed state in which the expandable structure does not project sufficiently beyond the outer surface of the sleeve to significantly obstruct passage of the distal end of the sleeve and expandable structure through a tissue incision approximately equal in diameter to the outer surface of the sleeve; structure for selectively placing the expandable structure in its expanded and collapsed states; a retaining collar having a tapered surface; and cooperating structure on the sleeve and collar for permitting movement of the collar relative to the sleeve towards the sleeve distal end so that the body tissue through which the sleeve is directed can be captured between the tapered collar surface and the expandable structure to thereby maintain the sleeve positively in its operative position.

This embodiment of the invention does not require a recess for accepting the expandable structure in its collapsed state, thereby eliminating the step of forming the recess in the sleeve.

In a preferred form, the expandable structure is a resilient membrane preformed to a distended shape corresponding approximately to the expanded state for the expandable structure While pre-forming of the membrane in a non-distended state is also contemplated by the invention, the distended formation is preferred in that once the membrane is placed in its expanded state, as through the introduction of a fluid, the walls of the membrane will remain unstretched and thus more rigid than if they were caused to be stretched by the expanding fluid. This results in more stable support of the sleeve on the tissue.

In a preferred form, the membrane is formed with a distended midportion and two integral collars which embrace the sleeve to maintain the membrane thereon. Preferably, an adhesive is employed to bond the membrane to the sleeve Solvent sealing, RF sealing, shrink bonding or a combination thereof are also contemplated by the invention.

Preferably, the sleeve is formed by a dip molding process. This allows for a thin walled membrane to be constructed which will collapse to a very low profile once the expanding fluid is withdrawn.

The invention also contemplates structure for facilitated positioning of the collar along the sleeve. Preferably, the collar has an annular configuration. A releasable spring member surrounds the collar and biasably urges the collar wall against the sleeve to thereby allow the collar to be held in a desired position. This spring is preferably a coil-type spring which can be loosened by enlarging the turns on the collar to allow repositioning of the collar.

The invention also contemplates a housing at the proximal end of the sleeve and defining a chamber in communication with the hollow sleeve passageway for introduction of a gas to distend the cavity bounded by the tissue in which the cannula is inserted. The housing defines an inlet opening in communication with the chamber which can be selectively blocked by a pivotable door, that has a flat wall and is preferably normally biased to a blocking position. The housing defines a seat around the inlet opening for sealingly accepting the flat door surface. The sealing surface defined by the housing is preferably disposed other than at a right angle to the length of the sleeve. This arrangement facilitates opening of the door upon the introduction of the spike/trocar and minimizes the contact period between the spike/trocar and door as the spike/trocar is fully extended into the sleeve.

Structure is also provided for manually pivoting the door, as for the purpose of releasing gas exhausted from the cavity through the housing. Preferably, a depressible button is provided on the housing that can be urged directly against the door. If a sealing gasket for the door is provided, the button is urged, through the sealing gasket, against the door. The door normally biases the button to an undepressed state.

The invention also contemplates a spike/trocar with a cap and cooperating structure to maintain the cap and housing in a predetermined relative position with the spike/trocar extended fully into the sleeve passageway. Preferably, the cap and housing are slidably engageable, one within the other. The housing preferably has a non-circular rim which is surrounded by a portion of the cap with the spike/trocar fully extended into the sleeve. Oppositely extending flanges on the cap are provided to facilitate withdrawal of the spike from the sleeve.

The present invention also contemplates a cannula for extension through tissue into a cavity, which cannula has: an elongate sleeve defining a hollow passageway through which a surgical instrument can be directed, with the sleeve being extendable through tissue into a body cavity and having a proximal end, a distal end, and an outer surface, with the distal end being positionable in the body cavity; expandable structure at the distal end of the sleeve for preventing withdrawal of the sleeve from an incision in tissue that is approximately equal in diameter to the diameter of the sleeve taken transversely of its length with the expandable structure in its expanded state, the expandable structure being collapsible so that it does not project from the outer surface of the sleeve sufficiently to significantly obstruct passage of the distal end of the sleeve out of an incision that is approximately equal in diameter to the dimension of the sleeve taken transversely of its length; a retaining collar having a tapered outer surface; and cooperating structure on the sleeve and retaining collar for permitting lengthwise movement of the collar along the sleeve to thereby permit capturing of the tissue between the tapered collar surface and the expandable structure.

In a preferred form, the sleeve is formed by extrusion. This facilitates inexpensive manufacture.

In a preferred form, the tapered surface of the collar has an annular shape with an included angle of approximately 30°.

BRIEF DESCRIPTION OF THE DRAWINGS

FIG. 1 is a section view of a laparoscopic cannula according to the present invention in operative position with respect to body tissue through which the cannula extends;

FIG. 2 is an enlarged section view of a membrane/balloon on the cannula for preventing withdrawal of the cannula from the tissue;

FIG. 3 is a section view of a piece of tissue with several cannulas according to the present invention extended through the tissue and each in operative position;

FIG. 4 is a section view of a modified form of cannula according to the present invention with a spike/trocar extended through a sleeve associated with the cannula;

FIG. 5 is a cross-sectional view of the sleeve taken along line 5—5 of FIG. 4;

FIG. 6 is a plan view of the cannula of FIG. 4; and

FIG. 7 is a section view of a still further modified form of cannula according to the present invention with a spike/trocar extended therethrough.

DETAILED DESCRIPTION OF THE DRAWINGS

In FIG. 1, a preferred form of laparoscopic cannula, according to the present invention, is shown at 10 in operative position with respect to body tissue 12, as for example the abdominal wall of a patient, through which the cannula 10 extends. The cannula 10 has a sleeve 14 with a proximal end 16, which remains externally of a patient and through which the cannula 10 is manipulated, and a distal end 18, which is directed into a cavity 20 through the tissue 12. The sleeve 14 defines a passageway 22 for communicating through the tissue 12 with the cavity 20.

To insert the sleeve 14 into the operative position of FIG. 1, a spike 24 is first directed through the sleeve passageway 22. An enlarged head 26 on the spike 24 arrests movement of the spike 24 through the cannula passageway 22 in a position wherein a sharpened end 28 of the spike 24 is exposed at the distal end 18 of the sleeve 14.

An incision (not shown) is made in the tissue 12. The sleeve 14 with the spike 24 therethrough is directed through the incision until the distal end 18 of the sleeve 14 is exposed in the body cavity 20.

To maintain the sleeve 14 in its operative position, the present invention contemplates the use of an inflatable membrane/balloon 30 at the distal end 18 of the sleeve 14 and a cooperating collar 32, surrounding the sleeve 14 and movable lengthwise relative thereto.

The details of the membrane are shown in FIG. 2. The membrane 30, which is preferably made from polyethylene teraphthalate, surrounds the distal end 18 of the sleeve 14 and resides within an annular recess 34 defined in the sleeve 14. In a collapsed state, as shown in phantom in FIG. 2, the membrane 30 has a compact profile and projects radially outwardly preferably not significantly further than the outer surface 36 of the sleeve 16. The compact storage of the membrane 30 permits the sleeve distal end 18 to be directed through the incision in the tissue 12 with minimal interference.

Once the membrane 30 is fully within the cavity 20, it can be inflated as through a syringe at 38 or through any other means, shown schematically in FIG. 1 at 39. The syringe 38 directs pressurized air or fluid radially outwardly of the sleeve 14 against the membrane surface 40. The membrane 30 is expanded sufficiently, as shown in FIGS. 1 and 2, that it prevents the sleeve 14 from being withdrawn from the tissue 12. An exemplary diameter of the expanded membrane 30 is 2.0 cm or greater, depending upon the diameter of the sleeve 14. An exemplary dimension of the expanded membrane 30 lengthwise of the sleeve 14 is 1-2 cm, again depending upon the sleeve and incision size. It is preferred to make the membrane 30 at least three times the size of the incision through which the sleeve 14 extends.

By exhausting air from the membrane chamber 42, the membrane 40 can be collapsed to facilitate withdrawal of the sleeve 14 through the incision. The details of the inflating/deflating mechanism at 44 will be described below.

The collar 32 has a tapered surface 46 which, with the membrane 30 inflated, is urged towards the membrane 30, thereby compressing the tissue 12 and capturing the tissue 12 in conjunction with the membrane 30. The collar surface 46 is shaped as a truncated cone. As seen in FIG. 1, a substantial area of tapered surface 46 is brought into contact with the tissue, thereby effecting a positive seal between the collar 32 and tissue 12.

The incline of the surface 46 is chosen so as to maximize contact area with the tissue without causing penetration thereof sufficient to contact and possibly rupture the membrane 30. In a preferred form of the invention, the angle a that the surface 46 makes with the axis of the cone is on the order of 15° or more. However, the angle may vary depending upon the thickness and nature of the tissue.

By reason of the substantial contact area between the surface 46 and tissue 12, it is possible to reorient the length of the sleeve 14 so that, for example, it is along the center lines 50, 52, without leakage of gas from the cavity 20. If the sleeve 14 is tipped so that it aligns with center line 50, the left side 54 of surface 46 tends to pull away from the tissue, yet not sufficiently that it disengages therefrom. Consequently, the seal remains intact entirely around the incision. The membrane 30 is sufficiently flexible to likewise conform to the inside surface 56 of the tissue 12 upon reorientation of the sleeve 14 and is sufficiently durable that it will not be prone to rupture when so deformed.

Because of the tapered configuration of the surface 46, a substantial amount of penetration can occur without traumatizing the tissue 12 around the incision. Once the collar 32 is appropriately positioned, a set screw 58 on the collar 32 can be tightened against the outer surface 36 of the sleeve 14. The sleeve 14 is thus positively maintained in the operative position of FIG. 1.

Another aspect of the invention is the provision of a door 60 to seal the passageway 22 in the absence of an instrument (not shown) or spike 24 being extended into the passageway 22. The door 60 is hingedly connected at 62 for pivoting movement relative to a radially enlarged flange 64 at the proximal end 16 of the sleeve 14. In the closed door position, a rounded projection 64 seats sealingly against a rim 66 on the flange 64. The closed door is intercepted by an instrument or the spike 24 being directed downwardly through the passageway 22 so that the door 60 is thereby pivoted to the open position in FIG. 1. Upon the instrument being removed, a spring 68 associated with the door 60 urges the door 60 back to its closed position. The door mechanism resides within a cavity 70 defined by a housing 72.

The cannula sleeve 14 is preferably defined in two parts. A first part 74 defines the passageway sealing structure including the door 60. The first sleeve part 74 remains externally of the patient at all times and is fabricated preferably mostly from medical grade stainless steel.

The second sleeve part 76 is directed through the tissue 12 and defines a conduit 78 through which the membrane 30 is selectively inflated and deflated. In a preferred form, the second sleeve part 76 is formed of plastic by extrusion. Fabrication from any other rigid material, such as fiberglass is also contemplated. The conduit 78 extending lengthwise of the sleeve part 76 can be formed in the extrusion process. The sleeve part 76 can be readily and economically manufactured so as to be disposable. It is thus possible to reuse the first part 74 and provide individually sterilized second parts 76, which are threadably connected at 80 to the first part 74. Other connections between the parts 74, 76 are also contemplated, such as bayonet, friction fit, etc.

The parts 76 can be made in a variety of lengths to be suitable for different types of operations and for different patients By minimizing the amount of projection of the part 76 into the cavity 20, the range of movement of the instruments in the cavity 20 is maximized.

The distal end of the second sleeve part 76 is undercut, as through the use of heat, to define the recess 34 and has a plurality of radially extending outlet ports 82 in communication with the conduit 78. Inflation and deflation of the membrane 30 is accomplished through the ports 82. The conduit 78 communicates through a chamber 84 on the sleeve part 74 with a conduit 86 integrally formed with the sleeve housing 72. The conduit 86 has a shut-off and/or one-way valve 88, which can be operated to prevent escape of air or fluid from the membrane chamber 42 with the membrane 40 inflated.

To place the cannula 10 in its operative position, the membrane 30 is deflated to the phantom position in FIG. 2. The spike 24 is directed through the cannula passageway 22 so that the spike end 28 projects from the distal end 18 of the sleeve 14. The spike 28 and surrounding sleeve are then directed through an incision in the tissue 12 until the recess 34 is entirely within the cavity 20. A valve 88 is opened and the syringe 38 or other pressurized air source is operated to inflate the membrane 30. Once the membrane 30 is fully inflated, the shut-off valve 88 can be closed to confine the air or fluid in the membrane 30. The spike 24 can then be removed from the sleeve 24 whereupon the door 60 closes to seal the passageway 22. The collar 32 is then urged towards the membrane 30, thereby compressibly capturing the tissue 12 in conjunction with the membrane 30. The set screw 58 is tightened to fix the location of the collar 32 and thereby maintain the cannula 10 in its operative position so that a desired instrument can be directed through the passageway 22 into the cavity 20.

To prevent escape of gas from the cavity 20 between the collar 32 and sleeve 14, a gasket 90 is provided on the end of the collar 32. A similar gasket 92 is provided at the proximal end 16 of the sleeve to sealingly cooperate with an instrument extended through the passageway 22.

FIG. 3 shows an arrangement of several of the cannulas 10 which may be simultaneously utilized during an operation. Relative orientations of the cannula 10 are fixed sufficiently that internal and external clashing between the cannulas 10 and any instruments extended through the sleeve 14 thereon is minimized.

BEST MODE FOR CARRYING OUT THE INVENTION

Referring initially to FIGS. 4-6, a cannula, according to the present invention, is shown at 110 in combination with a spike/trocar 112. The cannula 110 consists of a cylindrical sleeve 114 defining a hollow passageway 116 through which the spike/trocar 112 can be directed. The sleeve 114 has expandable means 118 at its distal end 120 and a housing 122 at its proximal end 124. The sleeve outer surface 126 slidably supports an annular collar 128 having a tapered annular surface 130 which, in conjunction with the expandable means 118, captively engages a tissue through which the cannula 110 is extended, to positively support the cannula 110 on the tissue.

The expandable means 118 consists of a resilient membrane 132 which surrounds the outer surface 126 of the sleeve 114. The membrane 132, shown in its expanded state in FIG. 4, is collapsible to a state shown in phantom in that same figure. The membrane 132 is preferably formed in a distended configuration. That is, it is molded about an element having a forming surface with a shape substantially the same as the shape of the membrane 132 in its expanded state. Preferably, the membrane 132 is made from PVC material by a dip molding process to produce a wall thickness of between 0.005-0.008 inches. The membrane 132 is formed with a distended midportion 134 and integral collars 136, 138 extending oppositely therefrom and closely embracing the outer surface 126 of the sleeve 114. The collars 136, 138 are preferably bonded to the sleeve 114 through the use of an adhesive or a solvent. The advantage of dip molding the membrane 132 in its distended state is that the membrane 132 can be placed in its expanded state without stretching the membrane 132. The wall of the membrane 132 thus retains its undeformed thickness and resultingly remains relatively rigid. At the same time, the membrane 132 is sufficiently thin that when the expanding fluid is withdrawn, it will collapse on itself closely against the sleeve outer surface 126.

Preferably, the expanding fluid for the membrane 132 is water or other incompressible fluid. An incompressible fluid is preferred because it rigidifies the membrane 132 in its expanded state to enhance the integrity of the support of the cannula 110. Further, water may block a leak that is sufficiently large to permit the flow of gas therethrough. Still further, water is preferred in that it provides a heat sink in operations which use lasers. Consequently, the integrity of the membrane will not degrade as readily from surrounding heat.

To introduce the fluid against the membrane 132 to effect expansion thereof, a lengthwise fluid passageway 140 is defined in the sleeve 114. To facilitate manufacture of the sleeve 114, the sleeve is formed by an extrusion process from rigid plastic, such as PVC. The passageway 140 is defined during the extrusion molding process through the entire length of the sleeve 114. The passageway 140 is blocked at the opposite sleeve ends 142, 144 by conventional means. A radial opening 146 extends through the sleeve wall 149 within the membrane 132 and into the passageway 140. A similar opening 148 is provided at the proximal end of the sleeve 114.

A one-way conventional syringe valve at 150 is provided to direct fluid from a supply 152 into the membrane 132 and withdraw the same therefrom. A flexible conduit 154 cut from micro-bore tubing is embedded in a neck 156 on the housing 122. The neck 156 surrounds and is secured to the sleeve 114. The conduit 154 establishes communication between the membrane 132 and syringe 150. A connector 158 has a tapered recess to accommodate a conventional syringe.

The details of the collar 128 are somewhat different than those of the previously described embodiment. The collar 128, which is preferably made from medical grade silicon, currently available from Dow Corning, has a conical body 159 with an integral locking portion 160. The locking portion 160 has a reduced diameter neck 162 which is surrounded by a coil-type spring 164. The spring 164 exerts a radially inward force on the underlying collar wall 166 which is thus borne against the outer surface 126 of the sleeve 114 to frictionally hold the collar 128 in a desired position along the sleeve 114.

The housing 122 has first and second joinable cup-shaped parts 168, 170, respectively, each preferably formed from ABS plastic. The part 168 has a through bore 72 with an entryway 174 that converges from left to right in FIG. 4 to smoothly guide the spike/trocar 112 into the center of the sleeve 114. The housing part 168 has an annular undercut 176 to closely accept a tapered, annular rib 178 on the housing part 170. An adhesive is used to bond the rib to the first housing part 168 within the undercut 176 to thereby hermetically seal the chamber 180 defined cooperatively by the first and second housing parts 168, 170.

The second housing part 170 has a through, entry opening 182 coincident with the axis of the sleeve 114. The housing part 170 has a boss 184 defining a seat 186 for a pivotable door 188 that selectively seals the opening 182. The door 188, which is preferably made from ABS plastic, is hinged at its one end 190 and biased by a coil spring 192 in a clockwise direction in FIG. 4 towards a blocking position in which it seals the entry opening 182. The seat 186 is generally planar to facially abut a planar surface 194 on the door 188. The plane of the seat 186 is disposed at other than a right angle to the axis of the sleeve 114 so that the incoming spike/trocar 112 encounters the surface 194 at an acute angle.

This arrangement has several advantages. First of all, it reduces the required range of pivoting for the door 188 to thereby simplify the construction of the spring 192. Further, less force is required to begin pivoting the door from its blocking position with the described arrangement. Further, the spike/trocar 112 remains in contact with the door 188 for a shorter time than if it would contact the door 188 at a right angle.

A closed cell foam plastic gasket 196 is disposed between the seat 186 and door surface 194 to enhance the seal at the entry opening 182. Preferably, the gasket 196 has a pressure sensitive adhesive on its upper surface 198 to facilitate assembly.

Means are provided at 200 for manually moving the door 188 in a counterclockwise direction out of its blocking position. The manual means 200 is a depressible button having a body 202 extendable through a bore in the housing wall 204. Spring loaded legs, with shoulders thereon (not shown provided at the bottom end of the button 200 to engage the wall 204 to allow press fitting of the button 200 so that the wall 204 is captive between the shoulders and an enlarged head 206 on the button 200. The bias of the door 188 in a clockwise direction in FIG. 4 places the button 200 in its undepressed state, shown in FIG. 4. Depression of the button 200, i.e. movement from left to right in FIG. 4, urges the free end of the button 200 against the door 188 and through gasket 196 to effect counterclockwise pivoting thereof, i.e. movement out of the blocking position.

The invention also contemplates the provision of a cap 208 bonded to the proximal end 210 of the spike/trocar 112. The cap 208 has a blind bore 212 for reception of the spike/trocar end 210. As seen in FIG. 6, the cap 208 has a generally rectangular configuration. The underside of the cap 208 is cup-shaped to surround a rim 214 of matching configuration on the housing 122. With the spike/trocar 112 fully extended into the sleeve 114, the cap 208 surrounds the rim 214 of the housing 122 and is effectively keyed thereto so that the relative position of the cap 208 and housing is fixed. Oppositely projecting flanges 216, 218 facilitate grasping and withdrawal of the spike/trocar 112.

To facilitate entry of the spike/trocar 112 into the entry opening 182 on the housing 122, the leading end 220 of the entry opening is funnel-shaped. A sealing gasket 222 is attached to a rim 224 and seals around the spike/trocar 112 which is squeezed therethrough as the spike/trocar 112 is directed into the sleeve 114.

FIG. 7 shows a modified form of cannula 226 according to the present invention. The cannula 226 is in most respects the same as that 110 in FIGS. 4-6. The principal difference is that the cannula 110 is configured for a 5 mm spike/trocar, whereas the spike/trocar 228 and cannula 226 is designed for an 11 mm spike/trocar. The diameter of all elements surrounding the sleeve 230, corresponding to the sleeve 114 in FIGS. 4-6, is changed to accommodate the larger spike/trocar 228.

The proximal end 232 of the spike/trocar 228 is tapered to have the same diameter as the end 210 of spike/trocar 212 in FIGS. 4-6. This allows use of the same cap 208 in the embodiments in each of FIGS. 4 and 7.

Another distinction between the cannula 226 and that 110 in FIG. 4 is that structure is provided at 234 on the cannula 226 for introducing gas into a chamber 236 in communication with the hollow passageway 238 on the sleeve 230. Once the spike/trocar 228 is removed from the sleeve 230, the structure 234 can be utilized to deliver $CO_2$ or other suitable gas from a supply 240 through a conduit 242 and in turn through the chamber 236 and passageway 238 into the cavity to which the cannula 226 is extended to effect expansion thereof.

The foregoing disclosure of specific embodiments is intended to be illustrative of the broad concepts comprehended by the invention.

We claim:

1. A cannula for extension through tissue into a cavity, said cannula comprising:
   a cylindrical sleeve defining a hollow passageway through which a surgical instrument can be directed,
   said sleeve having (a) a proximal end to be manipulated by a user in directing the sleeve into an operative position through body tissue into a body cavity, (b) a distal end which projects into a body cavity with the sleeve in its operative position and (c) a cylindrical outer surface;
   expandable means at the distal end of the sleeve for preventing withdrawal of the sleeve from a tissue with the expandable means in an expanded state,
   said expandable means being collapsible from its expanded state, wherein it projects radially sufficiently to prevent passage through an incision having a diameter approximately equal to the diameter of the outer cylindrical surface of the sleeve, to a collapsed state in which the expandable means does not project sufficiently beyond the outer surface of the sleeve to significantly obstruct passage of the distal end of the sleeve and expandable means through an incision in tissue approximately equal in diameter to the outer surface of the sleeve;
   means for selectively placing the expandable means in the expanded and collapsed state;
   a retaining collar having a tapered surface; and
   cooperating means on the sleeve and collar for permitting movement of the collar relative to the sleeve towards the sleeve distal end whereby body tissue through which the sleeve is directed can be captured between the tapered collar surface and the expandable means to thereby maintain the sleeve in its operative position.

2. The cannula according to claim 1 wherein the expandable means comprises a resilient membrane.

3. The cannula according to claim 1 wherein the expandable means comprises a resilient membrane preformed in a distended shape corresponding approximately to the expanded state for the expandable means.

4. The cannula according to claim 1 wherein the expandable means comprises a resilient membrane with a distended midportion corresponding in shape to the expanded state of the expandable means, and first and second collars integrally formed with and extending oppositely from the midportion of the expandable means for embracing the outer sleeve surface to hold the expandable means thereon.

5. The cannula according to claim 4 wherein at least one of the collars on the expandable means is bonded to the sleeve.

6. The cannula according to claim 1 wherein the expandable means comprises a membrane that is dip molded in liquid PVC material.

7. The cannula according to claim 1 wherein the retaining collar has an annular wall that surrounds the sleeve and outer surface and guides relative axial movement of the collar along the sleeve outer surface and a releasable spring member extends around the annular collar wall and urges the wall against the sleeve outer surface to hold the collar in any of a number of selected positions along the sleeve.

8. The cannula according to claim 1 wherein the cannula has a housing at its proximal end connected to the sleeve, said housing defining a chamber in communication with the sleeve hollow passageway, said housing having an inlet opening and means are provided for selectively blocking the inlet opening.

9. The cannula according to claim 8 wherein the blocking mean comprises a door that is movable between a blocking position and an open position and including spring means for biasing the door towards its blocking position.

10. The cannula according to claim 9 wherein the inlet opening axially coincides with the hollow sleeve passageway, the door has a substantially flat surface, the housing defines a seat surrounding the inlet opening against which the flat surface of the door abuts with the door in its blocking position, and with the door in its blocking position the plane of the flat door surface is at other than a right angle to the longitudinal axis of the sleeve.

11. The cannula according to claim 9 wherein means are provided on the housing for manually moving the door out of its blocking position to unblock the inlet opening.

12. The cannula according to claim 11 wherein the manual door moving means comprises a depressible button that is engaged by and normally urged to an undepressed state by the door in its blocking position.

13. The cannula according to claim 8 in combination with a spike/trocar having a cap thereon, there being cooperating means on the cap and housing for keeping the cap and housing in a predetermined relative position with the spike extended fully into the sleeve passageway.

14. The cannula according to claim 13 wherein the cap and housing are slidably engageable, one within the other.

15. The cannula according to claim 14 wherein the housing has a non-circular rim which is surrounded by a portion of the cap with the spike/trocar fully extended into the sleeve passageway.

16. The cannula according to claim 13 wherein the cap has oppositely extending flanges to facilitate withdrawal of the spike from the sleeve passageway.

17. A cannula for extension through tissue into a cavity, said cannula comprising:
   an elongate sleeve defining a hollow passageway through which a surgical instrument can be directed,
   said sleeve being extendable through tissue into a body cavity and having (a) a proximal end, (b) a distal end which is positionable in a body cavity, and (c) an outer surface;
   expandable means at the distal end of the sleeve for preventing withdrawal of the sleeve from an incision in tissue that is approximately equal in diameter to the dimension of the sleeve taken transversely of its length, with the expandable means in an expanded state,
   said expandable means being collapsible so that it does not project from the outer surface of the sleeve sufficiently to significantly obstruct passage of the distal end of the sleeve out of an incision that is approximately equal in diameter to the dimensions of the sleeve taken transversely of its length;

a retaining collar having a tapered outer surface; and cooperating means on the sleeve and collar for permitting lengthwise movement of the collar along the sleeve to thereby permit capturing of a tissue through which the sleeve extends between the tapered collar surface and the expandable means.

18. The cannula according to claim 17 wherein the expandable means has a cylindrical cross section.

19. The cannula according to claim 17 wherein the sleeve completely surrounds the outer surface of the sleeve.

20. The cannula according to claim 17 wherein the sleeve is formed by extrusion.

21. The cannula according to claim 17 wherein the collar has an annular shape surrounding the sleeve and the tapered surface defines an included angle of approximately 30°.

* * * * *